(12) United States Patent
Krawchuk

(10) Patent No.: US 11,357,268 B2
(45) Date of Patent: *Jun. 14, 2022

(54) SWADDLING GARMENT

(71) Applicant: Big Beings USA Pty Ltd., Zetland (AU)

(72) Inventor: Hana-Lia Krawchuk, Maroubra (AU)

(73) Assignee: BIG BEINGS USA PTY LTD, Zetland (AU)

(*) Notice: Subject to any disclaimer, the term of this patent is extended or adjusted under 35 U.S.C. 154(b) by 555 days.

This patent is subject to a terminal disclaimer.

(21) Appl. No.: 14/935,929

(22) Filed: Nov. 9, 2015

(65) Prior Publication Data

US 2016/0128392 A1    May 12, 2016

Related U.S. Application Data

(63) Continuation-in-part of application No. 12/920,034, filed as application No. PCT/AU2010/000800 on Jun. 25, 2010, now Pat. No. 9,179,711.

(30) Foreign Application Priority Data

Jun. 30, 2009    (AU) .................... 2009903034

(51) Int. Cl.
| | |
|---|---|
| *A41B 13/06* | (2006.01) |
| *A47G 9/08* | (2006.01) |
| *A61F 5/37* | (2006.01) |

(52) U.S. Cl.
CPC ............. *A41B 13/06* (2013.01); *A47G 9/083* (2013.01); *A61F 5/37* (2013.01)

(58) Field of Classification Search
CPC ...... A47D 15/02; A47D 15/005; A41B 13/06; A41B 13/08; A41B 13/065; A41D 11/00; A41D 13/1272; A47G 9/083; A47G 9/068; A61F 5/37
USPC .................... 2/69.5, 70, 75, 80, 83; 128/873
See application file for complete search history.

(56) References Cited

U.S. PATENT DOCUMENTS

| | | | |
|---|---|---|---|
| 1,956,813 A | 5/1934 | Stephenson | |
| 2,225,884 A * | 12/1940 | Parks ................... | A47D 15/008 2/114 |
| 2,579,276 A | 12/1951 | Schworm | |
| 2,675,557 A | 4/1954 | Kempner, Jr. | |
| 3,259,126 A | 7/1966 | Greiert | |

(Continued)

FOREIGN PATENT DOCUMENTS

| | | | |
|---|---|---|---|
| AU | 2004200438 | 8/2005 | |
| AU | WO 2007098558 A1 * | 9/2007 | ........... A41B 13/005 |

(Continued)

OTHER PUBLICATIONS

"Merriamwebster definition resilient.pdf".

(Continued)

*Primary Examiner* — Caitlin A Carreiro
(74) *Attorney, Agent, or Firm* — Bookoff McAndrews, PLLC

(57) ABSTRACT

A new or alternative swaddling garment that swaddles infants by sufficiently restraining movement of the limbs to suppress the startle reflex, yet allowing movement of hand to mouth thereby facilitating non-nutritive sucking and allowing the infant to self-soothe by sucking the hands or the fabric of the garment.

22 Claims, 8 Drawing Sheets

(56) References Cited

U.S. PATENT DOCUMENTS

| | | | |
|---|---|---|---|
| D269,474 S | 6/1983 | Mundy | |
| 4,611,353 A | 9/1986 | Als et al. | |
| D380,589 S | 7/1997 | Westman | |
| 5,722,094 A | 3/1998 | Ruefer | |
| D400,688 S | 11/1998 | Federspiel | |
| D457,288 S | 5/2002 | Westman | |
| 7,076,819 B2 | 7/2006 | Trani et al. | |
| 7,111,344 B2 | 9/2006 | French | |
| 7,181,789 B2 | 2/2007 | Gatten | |
| 7,587,769 B1 | 9/2009 | McDermott | |
| 8,191,189 B1 | 6/2012 | Spell | |
| 8,943,615 B2 | 2/2015 | Howard et al. | |
| 8,943,625 B2 | 2/2015 | Gotel et al. | |
| D883,613 S | 5/2020 | Damir et al. | |
| 2003/0131411 A1* | 7/2003 | Gibson | A41B 13/06 5/482 |
| 2005/0150047 A1 | 7/2005 | Trani et al. | |
| 2006/0016005 A1 | 1/2006 | Roda | |
| 2006/0064794 A1* | 3/2006 | Howard | A41B 13/08 2/69 |
| 2006/0150330 A1 | 7/2006 | Gatten | |
| 2009/0064390 A1* | 3/2009 | Beiring | A41D 27/085 2/80 |
| 2009/0099632 A1 | 4/2009 | Krier | |
| 2009/0282599 A1 | 11/2009 | Comerford | |
| 2011/0179546 A1 | 7/2011 | Millette et al. | |
| 2011/0180079 A1 | 7/2011 | Krawchuk | |
| 2012/0125347 A1 | 5/2012 | Soileau | |
| 2012/0284922 A1 | 11/2012 | Gangan et al. | |
| 2012/0311762 A1 | 12/2012 | Aiken et al. | |
| 2013/0139290 A1 | 6/2013 | Barski | |
| 2013/0269080 A1 | 10/2013 | Parker | |
| 2013/0333113 A1 | 12/2013 | Gotel et al. | |
| 2015/0335853 A1 | 11/2015 | Orewiler et al. | |
| 2018/0007976 A1 | 1/2018 | Lager | |
| 2018/0332902 A1 | 11/2018 | Damir et al. | |
| 2019/0208831 A1 | 7/2019 | Joshi | |
| 2019/0254355 A1 | 8/2019 | Griffin | |
| 2019/0297954 A1 | 10/2019 | Damir et al. | |
| 2020/0146370 A1 | 5/2020 | Bortone | |
| 2020/0196685 A1 | 6/2020 | Williams | |
| 2021/0007420 A1 | 1/2021 | Gangan et al. | |
| 2021/0022414 A1 | 1/2021 | Shekhani | |
| 2021/0030076 A1 | 2/2021 | Lee | |
| 2021/0259329 A1 | 8/2021 | Kiik-Miley et al. | |

FOREIGN PATENT DOCUMENTS

| | | | |
|---|---|---|---|
| AU | 2010212430 A1 | 1/2011 | |
| AU | 2011200705 B2 | 9/2011 | |
| CN | 2302668 Y | 1/1999 | |
| CN | 201150266 Y | 11/2008 | |
| CN | 104507338 A | 4/2015 | |
| GB | 2515400 A | 12/2014 | |
| NL | 1029033 C2 | 6/2007 | |
| WO | 2007098558 A1 | 9/2007 | |
| WO | WO-2007098558 A1 * | 9/2007 | A41B 13/005 |

OTHER PUBLICATIONS

Merriam-Webster definition of "Resilient"; www.merriam-webster.com/dictionary/resilient; accessed Jun. 30, 2012.
ErgoPouch, Healthy Sleeping, http://www.ergopouch.com.au/swaddle.html.
Woombie, Swaddle Snuggle Sleep, http://www.thewoombie.com.au.
Bregje E. van Slewen, et. al, Swaddling: A Systematic Review, 120:4 Pediatrics e1097 (Oct. 4, 2007) ("Swaddling: A Systematic Review").
E A Mitchell, et. al, Dummies and the Sudden Infant Death Syndrome, 68 Archives of Disease in Childhood, 501 (1993) ("Dummies and the Sudden Infant Death Syndrome.").
Barbara A. Hotelling, Newborn Capabilities: Parent Teaching Is a Necessity, 13:4 J. of Perinatal Edu. 43 (Fall 2004).
Joint Status Report for Dec. 9, 2020; Patent infringement suit re: U.S. Pat. No. 9,179,711; Civil Action No. 20-cv-10101-IT; United States District Court District of Massachusetts; *Big Beings USA Pty Ltd, and LB Online & Export Pty Ltd d/b/a Love to Dream Online and Exports* (Plaintiffs) v. *Nested Bean, Inc.* (Defendant).
Inter Partes Review of U.S. Pat. No. 9,179,711 B2; Case IPR2020-01234; *Nested Bean, Inc.* (Petitioner) v. *Big Beings USA Pty Ltd and LB Online & Export Pty Ltd d/b/a Love to Dream Online and Exports* (Patent Owner).
Australian Office Action dated Sep. 24, 2010, in Australian Patent Application No. 2010212430 (3 pages, in English).
Chinese Office Action dated Jun. 13, 2016 in counterpart Chinese Patent Application No. 201680077762.9 (12 pages, in Chinese with English translation).
Extended European Search Report dated Jun. 21, 2013 in counterpart European Patent Application No. 10793413.5 (3 pages, in English).
Extended European Search Report dated Feb. 1, 2018 in counterpart European Patent Application No. 17207995.6 (8 pages, in English).
International Search Report dated Aug. 23, 2010 in counterpart International Patent Application No. PCT/AU2010/000800 (4 pages, in English).
International Search Report dated Feb. 3, 2017 in counterpart International Patent Application No. PCT/IB2016/001652 (5 pages, in English).
Patent Trial and Appeal Board. *Nested Bean, Inc.* v. *Big Beings USA Pty Ltd. and LB Online & Export Pty Ltd., d/b/a Love to Dream Online and Exports*. Jan. 24, 2022. Judgment. (71 pages, in English).
Australian Office Action dated Dec. 1, 2010 in counterpart Australian Patent Application No. 2010212430 (3 pages, in English).
Chinese Office Action dated Jan. 7, 2020 in counterpart Chinese Patent Application No. 201680077762.9 (7 pages, in Chinese with English Translation).
Chinese Office Action dated Mar. 23, 2020 in counterpart Chinese Patent Application No. 201680077762.9 (12 pages, in Chinese with English translation).
Chinese Notification of Reexamination dated Jan. 5, 2022 in counterpart Chinese Application No. 201680077762.9 (15 pages, in Chinese with English translation).
Blair, "Sudden infant death syndrome: problems, progress and possibilities" Arch Dis Child 2002; 86:453-455, vol. 86, Jun. 1, 2002.
Summa Health, "Summa Uses Developmental Care with Premature Babies" PR Newswire, Oct. 22, 1998.
Brown, Louise, "Persistent crying isn't colic" Toronto Star, Feb. 16, 1993.

* cited by examiner

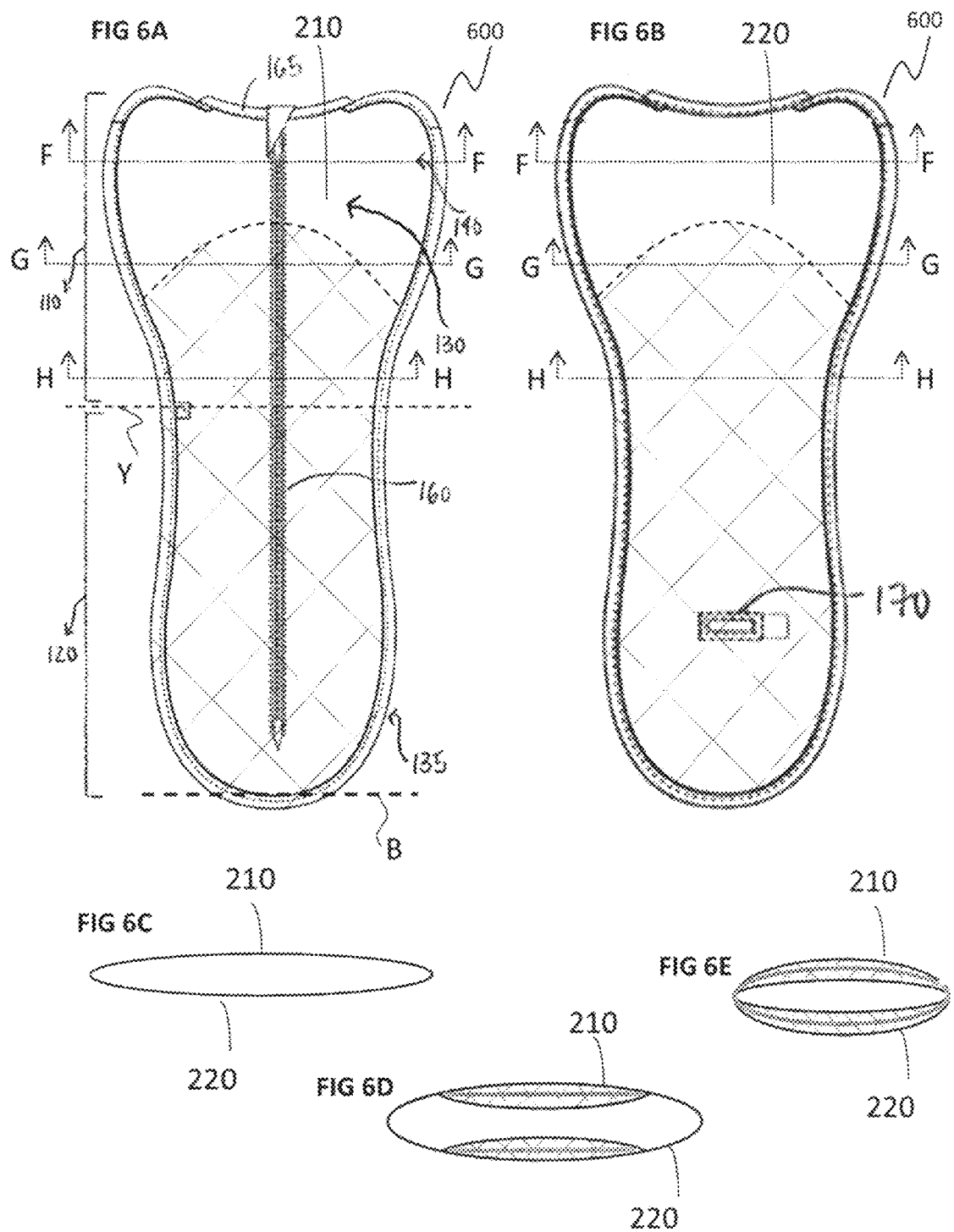

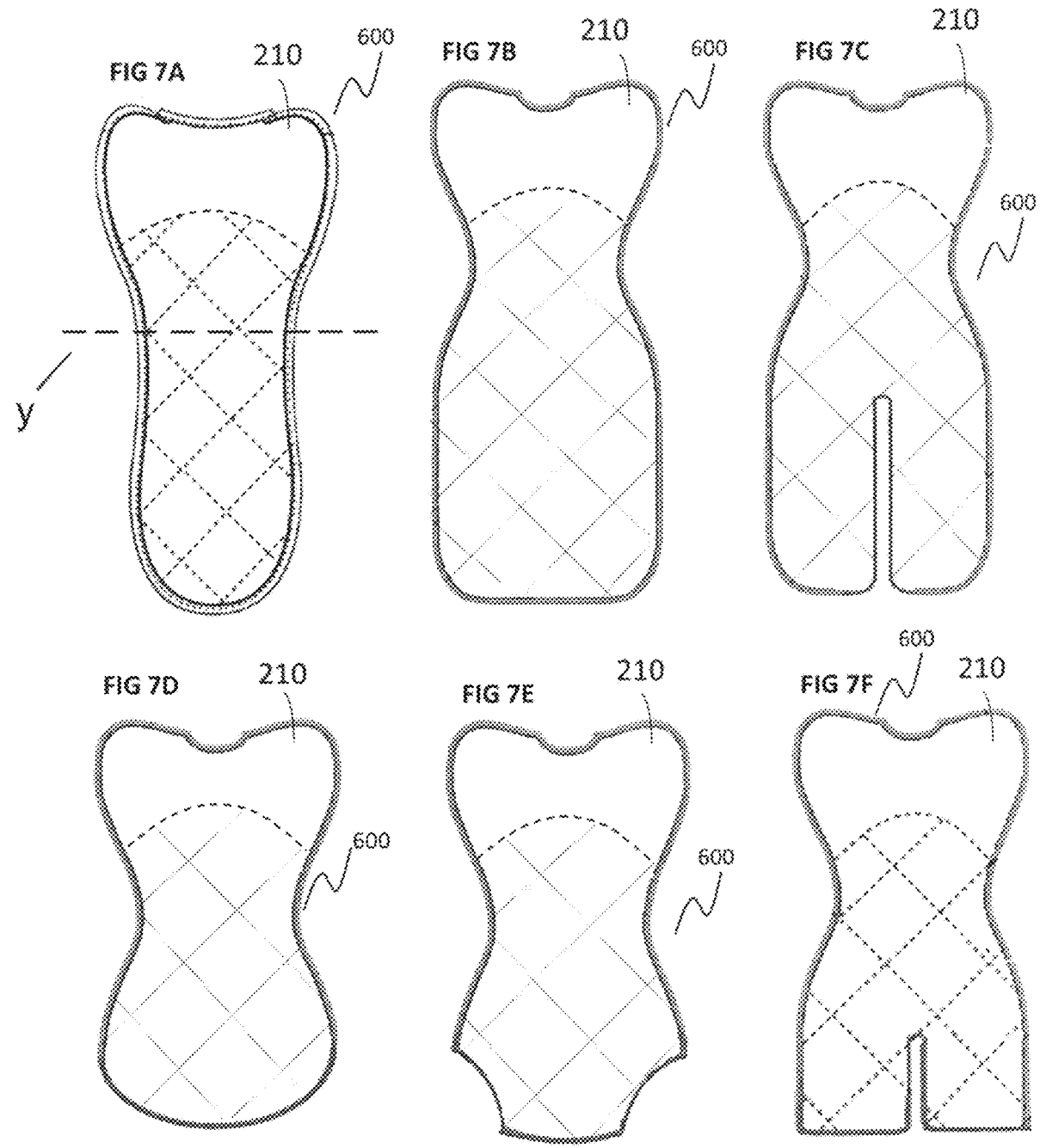

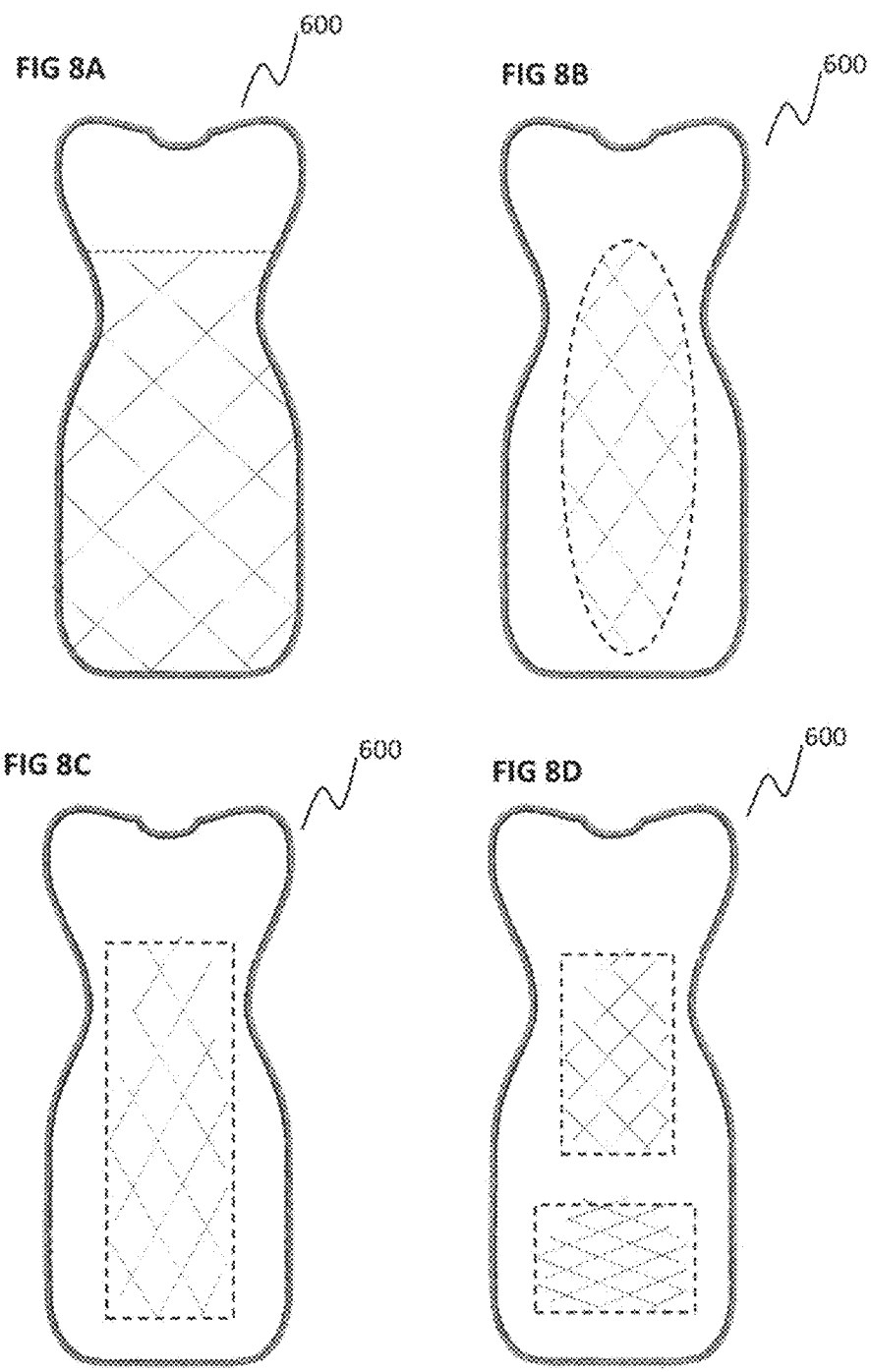

SWADDLING GARMENT

This application is a continuation-in-part (CIP) application of U.S. application Ser. No. 12/920,034, filed on Aug. 27, 2010, which is incorporated herein by reference.

TECHNICAL FIELD

The present invention relates to swaddles for infants, and in particular to swaddle garments.

The invention has been developed primarily for use as a means for swaddling infants for safe sleeping. However, it will be appreciated that the invention is not restricted to this particular use.

BACKGROUND

It is now well established that putting an infant to sleep on his or her back is the single most important step in reducing the risk of sudden infant death syndrome (SIDS).

Recent research also suggests that a baby's risk for SIDS can be greatly reduced by using a pacifier. Medical research also shows that babies who can satiate their natural sucking reflex sleep better. Experts recommend giving babies a pacifier every time they are placed to sleep. The exact reason that pacifiers reduce the risk of SIDS is not known. One suggestion is that the presence of a pacifier in the mouth may discourage babies from turning over onto their tummy because turning or moving may dislodge the pacifier. Another suggestion is that pacifier use and/or the sucking reflex helps keep the tongue positioned forward, keeping the airways open. Yet another suggestion is that pacifiers stimulate upper airway muscles and saliva production, so using pacifiers may keep babies from falling into a deep sleep, which is protective against SIDS.

One of the factors that has led to a revival in the ancient practice of swaddling is the practice of putting babies to sleep on their backs as this helps to reduce the incidence of SIDS. However, babies tend to sleep better on their tummies than on their backs. Swaddling has been found to assist infants sleep more comfortably on their backs and to assist in easing colic (particularly if swaddled with a little added tightness around the belly region for gentle pressure on or around the belly), which also improves sleep. Swaddling is the practice of wrapping infants tightly in a blanket or cloth so that movement of the limbs is restricted.

Medical research has shown that swaddling and sleeping supine (on the back) promotes more efficient sleep, with fewer spontaneous awakenings compared with sleeping supine but unswaddled. Swaddling seems to inhibit each step from sighs through startles to full arousal in the arousal pathway. This results in swaddled babies sleeping longer and being more likely to return to sleep on their own: *Swaddling: a systematic review*, Bregje E. van Sleuwen, et al, Pediatrics vol 120, number 4, October 2007.

To achieve the benefits of swaddling, infants need to be wrapped sufficiently tight to restrain the limbs and inhibit the movements associated with a full startle reflex, which can wake babies from sleep. The startle reflex is seen in infants from birth to around 6 months of age (some sources indicate it can occur in infants as old as eight months). The startle reflex is a natural reflex that babies are born with, and can be triggered by loud noise or sudden movement. In response to the trigger, the baby throws back his/her head, extends out the arms and legs, cries, then pulls the arms and legs back in. A baby's own cry can trigger the reflex. It can also be triggered during sleep, causing the baby to wake.

Care needs to be taken not to swaddle too tightly because this can compress the chest and make breathing difficult. There is also an increased risk of overheating especially when the head is covered or when there is infection. Improper swaddling can also lead to a risk of hip dysplasia (including hip dislocation) especially when swaddling with the hips and legs in extension and adduction (i.e. drawn toward the midline or sagittal plane of the body).

Other risks associated with swaddling babies includes an increased risk of SIDS when a swaddled infant is placed prone (on his or her front) or able to turn to prone position. The SIDS risk seems to be increased by swaddling with the head covered. There is also a slightly increased risk of acute respiratory infections, which seems to be related to the tightness of swaddling. These are discussed in the systematic review of swaddling referred to above.

Therefore, to swaddle properly and effectively, and to achieve the desired result, the blanket must be snug enough to immobilise the infant's arms, and to a certain degree its legs, but loose enough that it is still comfortable and not increase the risk of hip dysplasia or suppressed respiration.

Many parents and carers experience difficulty with swaddling due to unfamiliarity with swaddling techniques. If not swaddled correctly, the infant often wriggles free of the swaddle thus becoming exposed to a risk of suffocation or SIDS-related issues due to loose bedding and unrestricted positioning of the infant. However, swaddling alone cannot eliminate these risks. This is especially true for infants that are more than around six weeks old, when they are stronger and more active than newborns. Even when swaddled tightly with all limbs securely enclosed, infants can potentially roll, becoming entrapped in the swaddling blanket or trapped face down while still wrapped in the blanket.

To overcome the difficulty faced by parents and carers in learning proper swaddling techniques and to address the problems of improper swaddling, various swaddling garments have been developed. Swaddling garments such as the infant safety suit of WO 2007/098558 (the Snuggo), the Ergococoon and the Woombi address the problems of wrapping too loosely or too tightly since the degree of wrapping is predetermined by the garment.

As mentioned above, recent evidence shows that sucking on a pacifier is protective against SIDS. In addition, supplemental non-nutritive sucking (that is, sucking in addition to that required for feeding) is known to help to soothe an infant. Researchers have discovered that there is a clear reflex connection between the hand and mouth of a human fetus as early as 12-14 weeks after conception, and that thumb sucking in utero is common. After birth, many infants continue to soothe themselves by sucking on their thumbs or fingers. A newborn's ability to get the hands up to his or her mouth and suck is seen as a positive ability of the infant to organize him or herself in a self-soothing way. This helps establish an infant's ability to independently cope with stress and frustration.

Thus it would be an advantage to have a swaddle garment that overcomes the problems of improper swaddling and also provides an opportunity for non-nutritive sucking. This would improve the calming effect of the swaddling garment, since research that indicates that multiple simultaneous measures such as swaddling and sucking (along with rocking, white noise and other interventions) have an additive calming effect on crying infants: Karp H, *Swaddling and excessive crying*, Journal of Pediatrics, July 2007, e2. None of the aforementioned swaddling garments facilitates non-nutritive sucking.

None of WO 2007/098558 (the Snuggo), the Ergococoon or the Woombi provide access to the hands while the infant is swaddled. Movement of the infant's arms in all three of these swaddling garments is restricted to 180 degrees below the shoulder line so the hands are restrained near the body but below the shoulder line, out of reach of the mouth.

U.S. Pat. No. 7,587,769 is a swaddling article including a blanket formed with opposed arm-receiving sleeves that attempts to facilitate non-nutritive sucking by securing a pacifier to the blanket, thus overcoming the problem of pacifiers falling out of an infant's mouth. The blanket incorporates a pacifier retaining structure to retain a pacifier relative to the blanket so that the pacifier is unable to fall away from the blanket. This keeps the pacifier positioned near the mouth when the blanket is wrapped around an infant so it is available for the infant to suck on at will. The pacifier retaining structure includes a flap of fabric secured to the upper edge of the swaddling blanket. The flap is drawn across the region of the baby's mouth.

A disadvantage of the swaddling article of U.S. Pat. No. 7,587,769 is that it relies on a pacifier to be secured to the blanket. Another disadvantage is that it essentially extends the blanket across the face (around the mouth region), which can be uncomfortable and covering the face during sleep increases the risk of SIDs. Yet another disadvantage is that the swaddle article is in the form of a modified blanket and so lacks the convenience and advantages of a swaddling garment for example, the risk remains that the swaddle may loosen through movement thus becoming less effective and also posing a suffocation risk.

While research indicates that there are benefits associated with non-nutritive sucking (e.g. pacifier use), it also indicates that pacifier use may be associated with problems including:
  interference with breast feeding,
  dependence on the pacifier (so the baby cannot sleep without one),
  an increased risk of middle ear infections, and
  dental problems associated with prolonged use (see http://www.mayoclinic.com/health/pacifiers/PR00067/METHOD=print).

Hence, despite the established benefits of pacifier use, many parents choose not to use pacifiers. Further, some infants simply do not take to pacifiers. In any event, so as to minimise interference with breastfeeding, the recommendation is to wait until nursing is going well (usually one month) before offering a pacifier. Thus pacifier use is not suitable for all infants and it would be an advantage to provide a means for non-nutritive sucking that does not rely on pacifier use.

Reflexes are set motor responses to specific sensory stimuli. Newborns have a hand-to-mouth reflex that is a natural instinct to get their hands to their mouths. Research indicates that this ability to access the hands for sucking is important for self-soothing. The hand-to-mouth reflex (along with the startle reflex) is one of a number of primitive reflexes present from birth or earlier. Primitive reflexes are thought to have provided evolutionary advantages to humans.

The somatosensory system is a complex system of receptors and processing centres that produce the senses including touch, motion perception (proprioception) and balance, and spatial perception of body parts (kinesthesia). The tactile or skin senses (that rely on skin sensors for touch and pressure) appear first during fetal development. The vestibular system, which is responsible for movement and balance perception, and the tactile (touch) sensors are highly developed in newborns.

The hand-to-mouth reflex goes with two reflexes that are considered essential to appropriate feeding responses in newborns: the rooting (or search) reflex and the sucking reflex. Both of these reflexes are triggered by a touch (including pressure) stimulus.

The rooting reflex occurs when the infant's cheek or corner of the mouth is touched or stroked. The infant's mouth opens to follow and "root" (search) in the direction of stroking or touch. Rooting helps the baby to become ready to suck. The suckling reflex is triggered by touching the mucous membranes on the inside of the mouth with any object. Both reflexes facilitate nursing.

In the hand-to-mouth reflex, when an infant's cheek is stroked, his or her mouth roots and the arm flexes. After hand and mouth find each other, the infant may suck energetically on the hands.

There is a need for a swaddling garment that does not suffer the disadvantages of a swaddling using a blanket and that effectively swaddles infants by sufficiently restraining movement of the limbs to suppress the startle reflex, yet still affords sufficient movement so that infants can get their hand(s) toward their mouth, so providing the opportunity for non-nutritive sucking without reliance on a pacifier.

U.S. Pat. No. 4,611,353 describes a swaddling garment in which an infant's arms are gently bound in a bent-elbow, hands-up position to inhibit the ability to fling open the arms without restricting arm movement. Binding of the arms in this manner is described as useful for holding a premature infant.

The BabySense Cuddlewrap is a blanket shaped to wrap an infant's arms tightly near to the body and face, again as a means for suppressing jerks of the arms and legs. However, neither the manufacturer of the BabySense Cuddlewrap nor the inventor of garment of U.S. Pat. No. 4,611,353 refer to the benefit of providing access to the hands for non-nutritive sucking while swaddled and neither swaddle addresses this need adequately.

While the swaddle of U.S. Pat. No. 4,611,353 is referred to as a garment, the part of the garment that is responsible for binding the arms in the manner described is two flaps of sufficient length to wrap around the infant and overlap each other, secured in place either by strips of hook and loop fasteners or simply by relying on the length of the flaps. Thus binding of the arms is achieved by a length of fabric in a manner analogous to a blanket. Loosening of the binding is possible with movement/wriggling of the baby—particularly in the embodiment that relies on the length of the flaps to secure the wrapping around the infant or where the hook and loop fastening is not sufficient to restrain loosening of the flaps through wriggling movement of the infant.

Therefore, the risks associated with use of swaddling blankets or cloths remain with both the BabySense Cuddlewrap and the swaddle of U.S. Pat. No. 4,611,353, including:
  1. wrapping too tightly so as to suppress respiration;
  2. overwrapping the infant in several layers of fabric so as to increase the risk of overheating (particularly as the preferred embodiment of U.S. Pat. No. 4,611,353 also includes a hood);
  3. loosening of the swaddle around the upper body will result in excess fabric around the upper body, posing a suffocation risk to the infant;
  4. the arms are only restrained so long as the swaddle remains tightly secured around the infant and loosening allows increasing movement of the arms;

5. the swaddle does not facilitate or maintain access to the hands, although access can initially be provided depending on how the hands are positioned when the infant is first swaddled.

Thus both U.S. Pat. No. 4,611,353 and the BabySense Cuddlewrap share many of the disadvantages of swaddling using a blanket, and do not act to secure the hands in position near the face to provide the opportunity for non-nutritive sucking without reliance on a pacifier.

It is an object of the present invention to provide a new or alternative swaddling garment that swaddles infants by restraining movement of the limbs and which overcomes the disadvantages of other swaddling garments by allowing movement of the hand towards the mouth and maintaining the hand in a position relative to the infant's face thereby facilitating non-nutritive sucking.

It would be an advantage if the garment was also constructed to add gentle pressure around the torso and specifically around the horizontal plane of the abdomen area, which has been found to assist in easing colic. There are swaddle blankets available that claim to soothe colic. However, these known swaddle blankets achieve their benefit for colic through wrapping—for example, the swaddle blankets of U.S. Pat. Nos. 6,868,566 and 7,043,785 each have more than one fabric layer to wrap round the infant from opposite directions, and the blanket of U.S. Pat. No. 7,076,819 relies on traditional swaddling method of wrapping the infant neatly but with lengths of fabric to allow size and tightness adjustments and also allowing tying or tucking to prevent unravelling. All of these swaddle blankets share the disadvantage of traditional swaddle blankets in that they still ultimately rely on wrapping technique and can be cumbersome to use, with various flaps of fabric for wrapping, typing or tucking. It would be useful to have a swaddle garment that avoids the need to rely on wrapping technique and that also assists to relieve the symptoms of colic.

SUMMARY OF THE INVENTION

According to an aspect of the invention there is provided a swaddling garment for swaddling an infant, including an upper portion for enclosing an infant's upper body, wherein the upper portion includes:

(a) a bodice portion; and (b) one wing portion on one side of the bodice portion and another wing portion on another side of the bodice portion, said one wing portion and said another wing portion extending laterally from the bodice portion at an uppermost portion of the garment and being large enough to completely surround and retain an infant's arm and hand with the hand accessible to the mouth while preventing full extension of the arm;

each of said one wing portion and said another wing portion having a wing tip at an uppermost and most lateral portion of each of the wing portions, and said swaddling garment being tapered in at a garment waist line below said wing portion to restrict movement of the infant's arms out of the wing portions and maintain the infant's hand in position accessible to the infant's face for non-nutritive sucking.

According to another aspect of the invention there is provided a swaddling garment for swaddling an infant, including an upper portion for enclosing an infant's upper body, wherein the upper portion includes:

(a) a bodice portion; and (b) at least one wing portion, each said at least one wing portion extending laterally from its respective side of the bodice portion and being large enough to completely surround and retain an infant's arm and hand with the hand accessible to the mouth.

Preferably, the garment is notionally demarcated into upper and lower portions by a garment waistline, the garment having an uppermost periphery at an uppermost end of the upper portion, and a lowermost periphery at a lowermost end of the lower portion, wherein the wing portion extends in length substantially from the uppermost periphery to the garment waistline, and wherein a distance as measured from a most lateral part of the wing to the garment waistline is smaller than a distance as measured from the uppermost periphery of the garment to the garment waistline, such that the wing portions restrict movement of the infant's arms away from the bodice portion while allowing movement of an infant's hand towards the infant's mouth for non-nutritive sucking.

The invention thus provides a new or alternative swaddling garment and method for swaddling that swaddles infants by sufficiently restraining movement of the limbs to suppress the startle reflex, yet allowing movement of the hand towards the mouth and maintaining the hand in position relative to the infant's face thereby facilitating non-nutritive sucking. In an embodiment, it also assists to relieve the symptoms of colic by applying gentle pressure around the torso and specifically around a horizontal plane corresponding with the abdomen area.

For a better understanding of the invention and to show how it may be performed, a preferred embodiment will now be described, by way of non-limiting example only, with reference to the accompanying drawings and example.

FIG. 6A is a front view of another embodiment.

FIG. 6B is a back view of the embodiment of FIG. 6A.

FIG. 6C is a cross section of the embodiment of FIGS. 6A and 6B, taken along lines F-F of FIGS. 6A and 6B.

FIG. 6D is a cross section of the embodiment of FIGS. 6A and 6B, taken along lines G-G of FIGS. 6A and 6B.

FIG. 6E is a cross section of the embodiment of FIGS. 6A and 6B, taken along lines H-H of FIGS. 6A and 6B.

FIG. 7A shows a front view of an additional embodiment in which the lower portion tapers in at the lowermost periphery.

FIG. 7B shows a front view of an additional embodiment in which the lower portion widens below the waist line.

FIG. 7C shows a front view of an additional embodiment in which the lower portion comprises pants.

FIG. 7D shows a front view of an additional embodiment in which the lower portion is open below the waistline.

FIG. 7E shows a front view of an additional embodiment in which the lower portion includes leg holes and a closeable opening at the lowermost periphery.

FIG. 7F shows a front view of an additional embodiment in which the lower portion includes shorts.

FIG. 8A shows a front panel of an embodiment, with a weighted portion configured in a horizontal plane around the abdomen.

FIG. 8B shows a front panel of an embodiment, with a weighted portion configured in an oval shape sitting over the front of the abdomen.

FIG. 8C shows a front panel of an embodiment, with a weighted portion configured in a rectangular shape sitting over the front of the abdomen; and, FIG. 8D shows a front panel of an embodiment, with a weighted portion configured in a first shape (drawn as rectangle) sitting over the front of the abdomen and a second weighted portion further down the lower portion of the garment.

EXAMPLE 1 is a method of swaddling an infant.

DESCRIPTION OF PREFERRED EMBODIMENTS

The invention provides a new or alternative swaddling garment that swaddles infants by sufficiently restraining movement of the limbs to suppress the startle reflex, yet allowing movement of the hand towards the mouth and maintaining the hand in position relative to the infant's face thereby facilitating non-nutritive sucking and allowing the infant to self-soothe by sucking the hands. In this way, the swaddling garment offers advantages over other swaddling garments by providing greater protection against sudden infant death syndrome (SIDS) by virtue of facilitating non-nutritive sucking.

Infants swaddled in the swaddling garment can act on the hand-to-mouth reflex (the natural instinct to get their hands to their mouths) as the swaddling garment allows movement of the hands towards the mouth. Further, the swaddle garment maintains the infant's hand(s) in position relative to the face, improving access to the hands and increasing the opportunity for movement of the hands and/or arms, or the fabric of the swaddling garment itself, to trigger the rooting reflex. This is the natural instinct of the infant to search for something to suck on when the cheek is touched or stroked. In this way, the swaddling garment is designed to facilitate non-nutritive sucking—on the hand(s) or on the fabric of the swaddle garment near the hand(s).

Referring to FIGS. 1A and 1B, front and back views are shown of a preferred embodiment of the swaddling suit/garment 100 (see FIGS. 1A and 1B, respectively). The swaddling garment 100 includes an upper portion 110 for at least partially enclosing the infant's upper body. As shown in FIG. 1A, the garment 100 has an uppermost periphery at the uppermost end of the upper portion (the end indicated by the line marked "A") and a lowermost periphery at the lowermost end of the lower portion (the end of the garment indicated by the line marked "B"). Persons skilled in the art will appreciate that the uppermost and lowermost peripheries are not linear but follow the top and bottom edges of the garment respectively (the lines marked "A" and "B" are indicative only of the "uppermost" and "lowermost" ends of the garment, respectively). Features bearing the same number or letter designations in any of the embodiments illustrated are the same as described in relation to any other embodiment.

Figure 1:
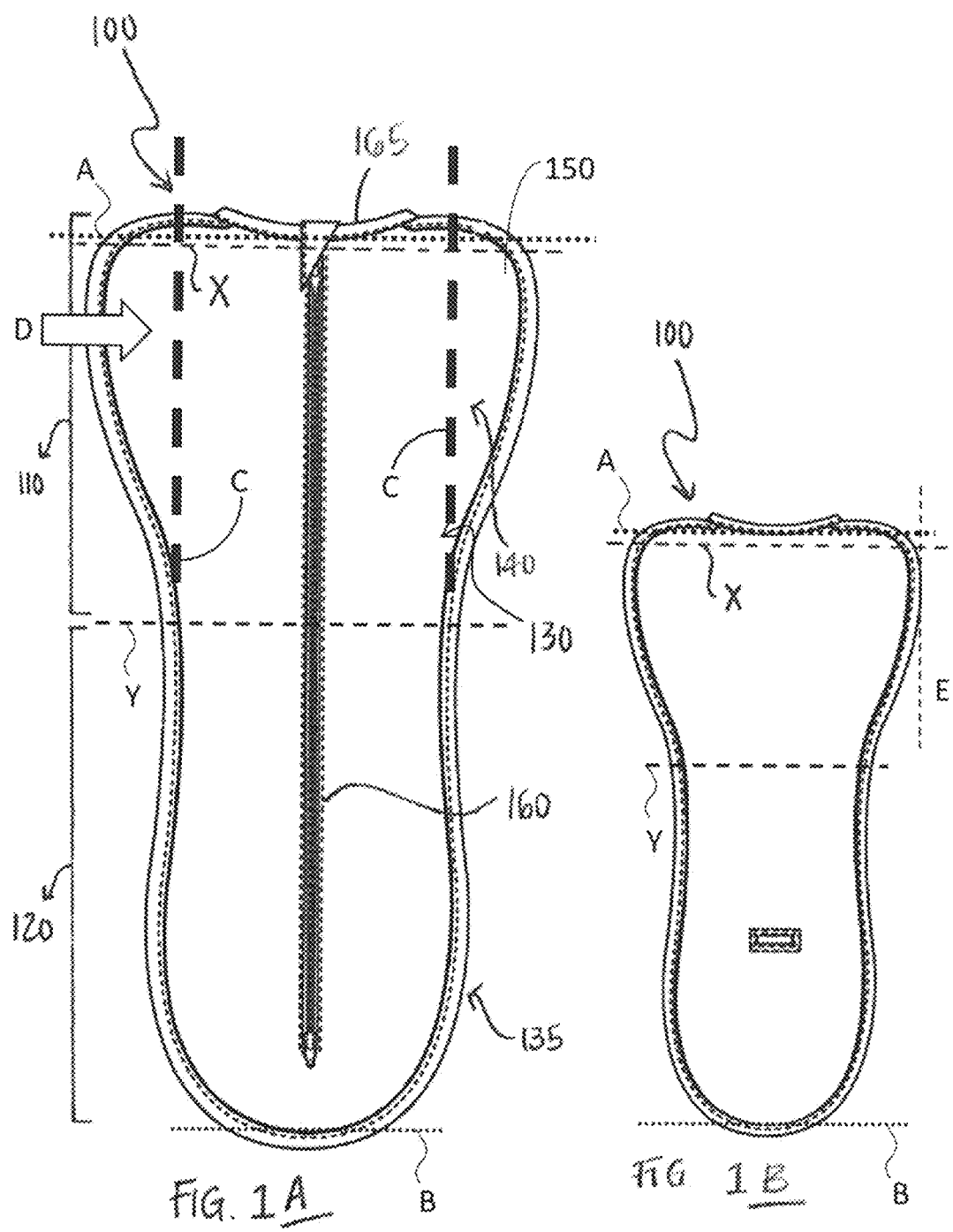
FIG. 1A is a front view of one embodiment of a swaddling garment.
FIG. 1B is a back view of the embodiment shown in FIG. 1A, shown in a smaller scale.

As shown in FIG. 1A, the garment 100 is notionally divided into an upper portion 110 and a lower portion 120 by a garment waistline (demarcated by line "Y"). The waistline "Y" of garment 100 notionally corresponds to the natural waist (as depicted in the drawings) but persons skilled in the art will appreciate that a garment waistline may vary in position from just below the bustline to just below the hipline. The upper portion (indicated by the bracket labelled 110 in the FIGS. 1A to 5B) is for enclosing the infant's torso and arms (the upper body).

Extending laterally away from the midline is a bodice portion 130 sized to enclose an infant's torso substantially without arms, wherein the bodice portion extends from a garment shoulder line to a garment waistline Y on each side of the bodice portion 130 is a wing portion 140 that is intermediate said wino portions, as can be seen in FIG. 1A. The wing portion 140 is the part of the upper portion lateral to the line marked "C" on each side of the garment 100. As shown in FIGS. 1A and 2A (for example), each wing portion 140 is large enough to completely surround and retain the infant's arm, such that said wino portions act as position-restricting means and extends in length:

(a) from the uppermost periphery of the garment (the edge of the garment near the end marked by line "A"—refer FIGS. 1A to 5B);

(b) substantially to the garment waistline (demarcated by line "Y" in FIGS. 1A to 5B).

The wing portions 140 restrict movement of the arms away from the bodice portion 130 (that is, away from the infant's torso, in the opposite direction than depicted by the arrow marked "D" in the figures). This restriction in arm movement is achieved by the proportions of the wing portions, better understood by reference to FIGS. 1A, 2A, 3A, 4A and 5A. The line marked "E" in each of FIGS. 1B to 5B represents a vertical plane corresponding to the most lateral part of the wing portion. The wing portions are of a dimension (measured to the most lateral part of the wing portion (at line "E") that prevents full extension of the arm. In an embodiment, by way of example only, this may be achieved by making the dimension from the most lateral part of the wing portion (at line "E") to the garment waistline smaller than the distance as measured from the uppermost periphery of the garment to the garment waistline (e.g. refer FIGS. 1A to 4). These dimensions reflect the relative proportions of what would be reflected in a conventional garment, respectively, as:

(a) the distance from the shoulder seam to the end of the sleeve; and (b) the length of the underarm seam.

Figure 4:
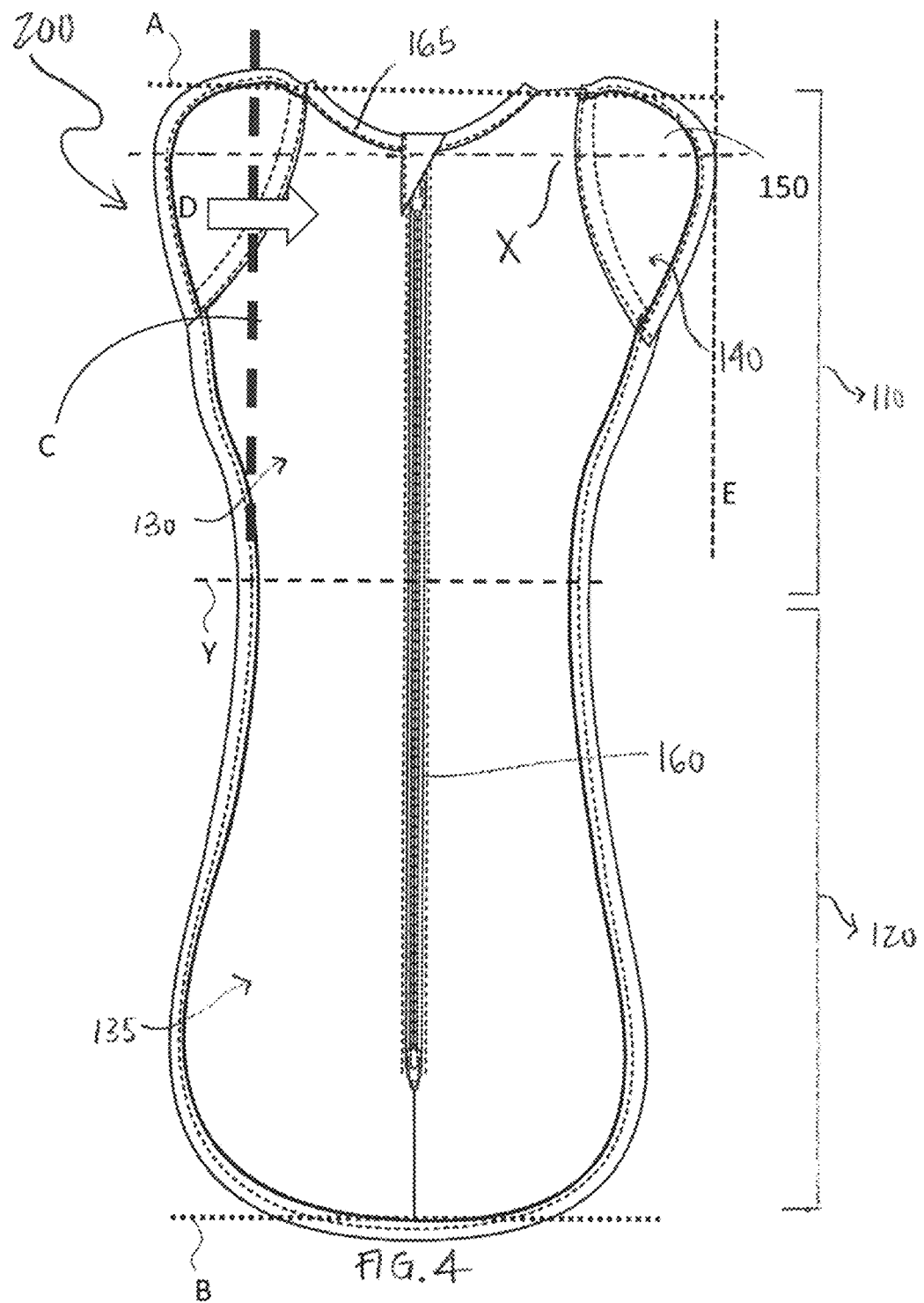
FIG. 4 shows a front view of the embodiment of FIG. 3A, showing the detachable wing portions attached.
Figures 5A, 5B:
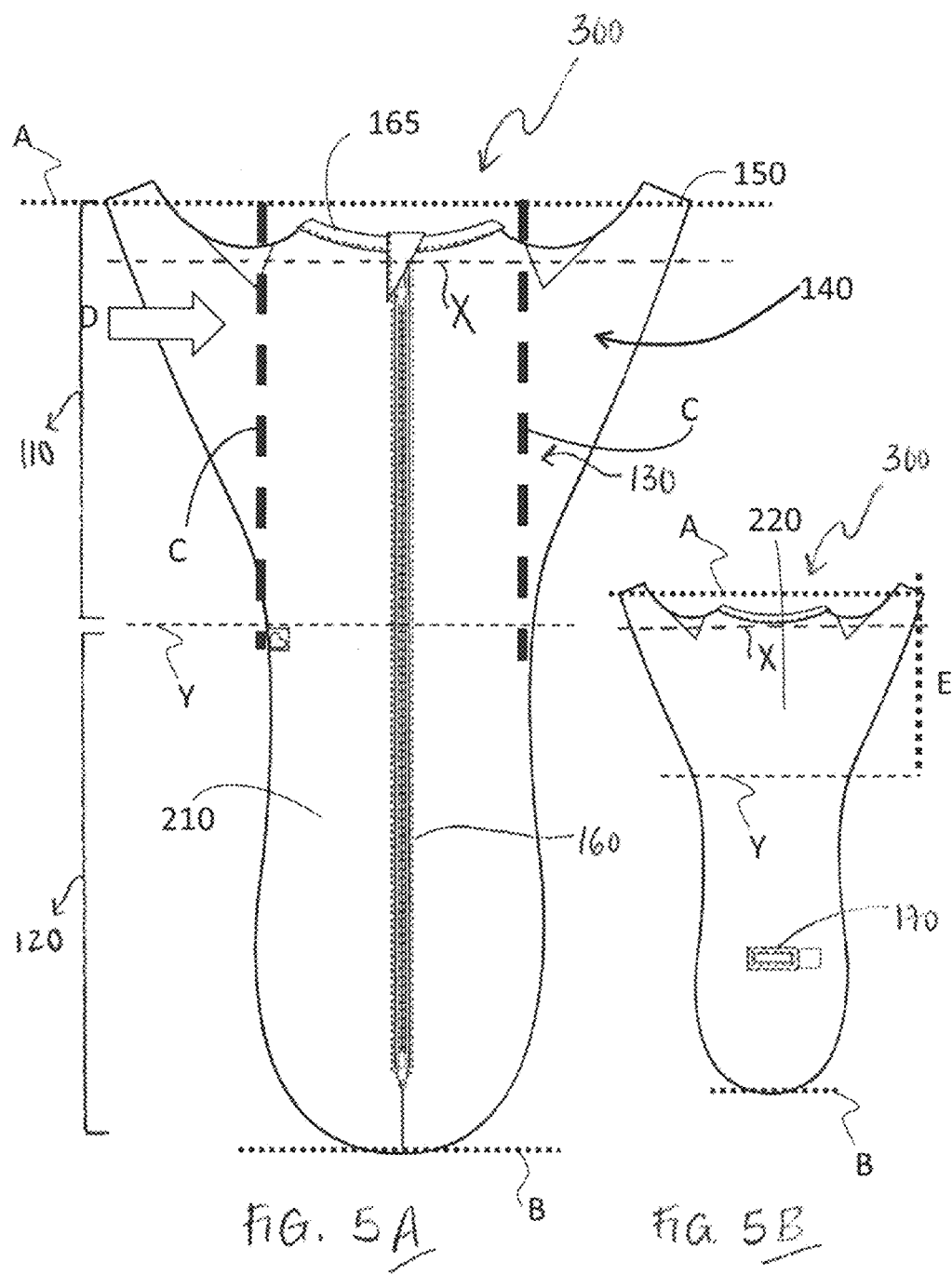
FIG. 5A is a front view of another embodiment.
FIG. 5B is a back view of the embodiment of FIG. 5A, shown in smaller scale.

The wing portion 140 prevents full extension of an arm enclosed therein, by being "shortened" relative to the length of an arm contained within the wing portion (whether achieved through the relative proportions of the wing portion to other parts of the garment, as illustrated in FIGS. 1A to 4 and described in the preceding paragraphs, or by other means, such as shortening of the "underarm "seam" (or equivalent) or the "shoulder seam" (or equivalent—as depicted in FIGS. 5A and 5B). Fabric tension restricts arm movement in a direction away from the bodice portion 130 so that an arm encased within the wing portion is prevented from extending out fully. Tapering in of the wing portion 130 at the garment waistline (demarcated by line "Y") prevents the arm from escaping out of the wing portion into the rest of the garment 100 (the same applies for embodiments 200 and 300). Slight resistance in the wing portions and retention of the whole arm and hand within the wing portion assists babies to feel their "edges", simulating the enclosed, comforting environment of the womb. The wing tip 150 acts like a "corner" (edge) to the environment to cover the hands. The feeling of fabric on the hand and the covering of the hand activates proprioception, giving feedback to the infant. As discussed below, the restriction in arm movement suppresses the startle reflex but still allows movement of the hand towards the mouth, so that baby can suck the hands for self-soothing.

The bodice portion 130 may be continuous or integral with the wing portions 140 (e.g. refer to FIGS. 1A and 1B, 2A and 2B, and 5A and 5B). Alternatively, the wing portions 140 may be discrete but connected to the bodice portion. In an embodiment, the most lateral part of the wing portion 140 is removable (see FIGS. 3A, 3B, 4A and 4B).

In all embodiments, the wing portions 140 restrict movement of the arms away from the bodice portion and prevent full extension of the arm, but permit arm movement towards the bodice portion 130 (in the direction depicted by the arrow marked "D" in FIGS. 1A, 2A, 4, and 5A), thereby allowing access of hands to the mouth for non-nutritive sucking.

As can be seen from FIGS. 1A and 1B, 2A and 2B, 4, and 5A and 5B, the garment is greater in width between the wing portions 140 than at the garment waistline (demarcated by line "Y"). In this way, the wing portions 140 form a T-like shape with the bodice portion 130. Referring to FIGS. 1A to 4, the garment may be rounded in shape, following the contours of an infant, with the T-like shape formed by the wing portions 140 extending laterally from the bodice portion 130 also being rounded, as can be seen in FIGS. 1A and 1*b*, 2A and 2B, 3A and 3B and 4. Referring to FIGS. 5A and 5B, the wing portions may be geometric rather than rounded in shape.

The common feature in all embodiments illustrated in FIGS. 1A to 5B is that the wing portions 140 extend laterally (i.e. outwardly) away from the midline to form the most lateral and widest portion of the swaddling garment 100. As depicted in the drawings, the wing portions 140 extend from approximately the waist line (demarcated by line "Y") of the garment 100 to the uppermost periphery of the garment 100 (at the uppermost end of the garment, demarcated by line "A").

The wing portion 140 acts as a position-restricting means to maintain the hands in position relative to the face by virtue of the following:

1. as can be seen from FIGS. 1A and 1B, each wing portion 140 is designed to completely surround and retain one of the infant's arms, with the hands accessible to the mouth, with wing tips for receiving the hands being positioned near or toward the horizontal plane of the shoulder line (e.g. as seen in FIGS. 1A and 1B) or above (e.g. as seen in FIGS. 2A and 2B) the horizontal plane of the shoulder line;

2. the wing portion 140 fits snugly around the arm thereby hugging the arm towards the bodice portion in the aforementioned position thereby maintaining the hands up near the face; and 3. the wing portion 140 is shaped to taper in towards the bodice portion near the garment waist line (refer line "Y" in FIG. 1) under the bent elbow, thereby cupping the bent elbow and further assisting to support the hands up near the face and to restrict the infant from moving the hands away from the face, by preventing passage of the arm out of the wing portion.

As can be seen in FIGS. 1A, 2A, 3A, 4A and 5A, the wing portion 140 includes a wing tip 150 at its outermost (most lateral) portion, to receive the infant's raised hand (refer Figures). The wing tip 150 assists to further secure the hand and retain it in place once in position. In one arrangement, the wing portion is resilient, the resilience further assisting to hug the arms towards the body and maintain the hand in position at the wing tip. The shape of the uppermost part of the upper portion also prevents the hands from travelling into the neck hole 165 (see inset, FIG. 3A), which can pose a choking risk to infants by restricting the neck hole 165.

In some arrangements, the wing portion 140 may include an internal pocket. The pocket may enclose the lower arm and hand, or just the hand in a glove-like fashion. This further assists in retaining the hand relative to the face.

The swaddling garment 100 facilitates non-nutritive sucking by the swaddled infant (and hence assists the infant to self-soothe by sucking the hands or the fabric of the swaddling garment near the hands) in the following ways:

1. the swaddling garment 100 makes the infant's hands accessible to the mouth by retaining the infant's hands in position relative to the face yet allowing the arms to move between adducted and abducted positions; and 2. the wing tip is configured so that it is able to brush or touch the infant's own cheek or the corner of his or her mouth when so moving the arm(s) and/or turning the head, thereby triggering the infant's rooting and/or hand-to-mouth reflexes.

By retaining the hand(s) near the mouth while allowing the infant to move the hand toward the mouth by adducting the arm and/or turning the head, the garment enables sucking of the hand(s) or fabric of the swaddling garment near the hands for self soothing (through non-nutritive sucking). Research has found that non-nutritive sucking is protective against SIDS. Known swaddling garments retain the hands away from the face by restricting movement of the hands to 180 degrees below the shoulder line. By restricting movement of the hand(s) to 180 degrees near or above the shoulder line, the swaddling garment 100 overcomes the problem of prior art swaddling garments that deny access of hands towards the mouth. This is achieved by the shape of the wing portions. Taking FIG. 2A as an example, tapering in of the upper portion 110 at the garment waistline (demarcated by line "Y") prevents the arm (which is wholly contained within the wing portion 140 in a hand-raised and elbow-bent position) from escaping out of the wing portion 140. This means the infant's hands are retained towards the uppermost periphery (near or towards the uppermost end of the garment 200 demarcated by line "A" in FIG. 2A) but can move towards the mouth for non-nutritive sucking. These features also apply to the other embodiments illustrated in FIGS. 1A and 1B, 4 and 5A and 5B).

A further advantage of the T-like configuration (greater width between wing portions 140 than at the garment waistline Y, as seen in FIG. 1A) with the wing portions retaining the arms and hands in the hands-raised position on both sides of the bodice portion is that the swaddled infant laid supine (on the back) for sleep is hindered from rolling over the arms into the prone (face down) position. This is further protective against the risk of SIDS.

Rolling is restricted by the positioning of the arms with elbows bent and hands up towards (FIG. 1A) or above (e.g. FIG. 2A) the shoulder line and to the side of the bodice portion (by virtue of the wing portions being lateral to the bodice portion). However, if babies do manage to roll onto their front then they can use their arms to push up off the mattress, turn their head and keep breathing, minimising suffocation risk. Stronger babies have the advantage of being able to push themselves back to the supine position. Known swaddle garments bind the arms to the chest, preventing the infant from being able to use the arms to push up off the mattress.

The lower portion 120 of the swaddling garment 100 includes a pouch 135 for enclosing the infant's legs. The swaddling garment 100 tapers in towards the garment midline at or near the waist line, just below the wing portion 140 (as can be seen in FIG. 1A). The garment 100 then widens to accommodate hip width and the lower portion 120 remains substantially the same width from around the hip down to the lowermost part (where the feet are enclosed). This is to ensure an even, snug fit of the swaddling garment 100 along the length of the infant.

The garment applies compressive pressure around the body, causing the garment 100 to hug the infant's contours. The compressive force assists to press the infant's arms towards the body. This provides resistance against full extension, thereby restricting movement of the infant's arms away from the body. In newborns, this wrapping of the infant's arms towards the body suppresses the full extensor startle response to loud noise or sudden movement. The startle response is the instinct of infants aged up to around 6 months to startle upon a loud noise or sudden movement, causing them to quickly spread out (extend) their limbs then draw (flex) them back in towards the body.

Thus the swaddling garment 100 confines the arms with hands towards (FIG. 1A) or above (FIG. 2A) the shoulder line and accessible to the face (mouth). The garment 100 also hugs the contours of the baby to further inhibit the startle response. The pressure applied by the swaddling garment 100 as it hugs the infant's contours also provides somatosensory (including proprioceptive) feedback to infants, assisting with infant's touch, movement and balance perception.

In one arrangement, the swaddling garment 100 shown in FIG. 1A is made of a resilient material with two-way stretch (that is, resilience in both warp and weft directions). In one arrangement, the material is a fabric containing a percentage of elasticated yarn such as cotton spandex. However, the swaddling garment can be made using any suitable material for wrapping an infant, so long as the configuration of parts and shape of the wing portions secure the arms in a hands-up position with the hands positioned relative to the face such that the hands are accessible to the mouth. The relative positioning of the hands to the mouth facilitates non-nutritive sucking and restricts movement of the arms and hands away from this position.

Extension of the limbs requires the infant to push against the compressive force applied by the garment 100 as it wraps around the infant. Where the garment 100 is made of resilient material, the resilience assists in tending the limbs towards the body by resisting full extension of the limbs while allowing the limbs to move between adducted and abducted positions (toward and away from the sagittal or longitudinal midline plane of the body). This further facilitates hand-to-mouth access by the infant. This is because the resilience further assists to maintain the hand relative to the face while permitting hand movement 180 degrees below the shoulder (the approximate position of the shoulder line is demarcated by the dashed line marked X in FIGS. 1A, 1B, 2A, 2B, 4 and 5A and 5B).

The swaddling garment 100 has an opening 160 to allow insertion of an infant into the garment. The opening 160 is closeable by any suitable closure means, including hook and loop fasteners, zipper means, buttons or any other method of fastening the opposing sides of the opening together. In the preferred embodiment, the opening 160 extends longitudinally along the swaddling garment 100, from the upper portion to the lower portion (see FIG. 1A). However, in some arrangements, the opening 160 may be shorter than is illustrated or be positioned elsewhere such as along a side seam or running along the lowermost seam of the lower portion 120.

In a preferred embodiment, the closure means is a two-way zipper extending along the opening, allowing the opening 160 to be partially openable from either end. Any other closure means (e.g. buttons, press studs) that allows partial opening from either end can also be used. When opened from the lower portion end, the opening 160 provides access to the infant's lower body (e.g. for changing nappies or using a child restraint in a car or pram) while the upper body remains swaddled. Alternatively, the closure means does not provide two-way access (not illustrated) but the opening is positioned such that access to the lower body is possible while the upper body remains swaddled (e.g. by positioning the opening with closure means along a seam).

In a preferred embodiment, the swaddling garment 100 comprises a front panel (FIG. 1A) secured to a back panel (FIG. 1B). The front panel is configured to cover the front of an infant enclosed within the garment, and the back panel is configured to cover the back of the infant. In some arrangements, the upper portion and lower portion are continuous, formed by front and back panels that extend the full length of the swaddling garment 100—as illustrated. In other arrangements, the front and/or back panels comprise adjoining subpanels that collectively extend the full length of the swaddling garment (not illustrated).

In the preferred embodiment, the opening 160 is positioned on the front panel of the swaddling garment 100 for example, as shown in FIG. 1A, extending lengthways along the centre of the front panel from the neck hole 165 to the lower portion of the garment 100. The opening can also be positioned off-centre or along a side seam.

Referring to FIG. 1B, a slot 170 allows passage of a child restraint belt (e.g. car seatbelt) through the garment 100. The slot 170 enables the belt to pass through the internal volume and exit through a corresponding portion of the opening 160. As the opening 160 can be partially opened, it can remain substantially closed while allowing the belt passage through the garment. This allows the infant to be secured for transportation while remaining swaddled.

Figure 2:
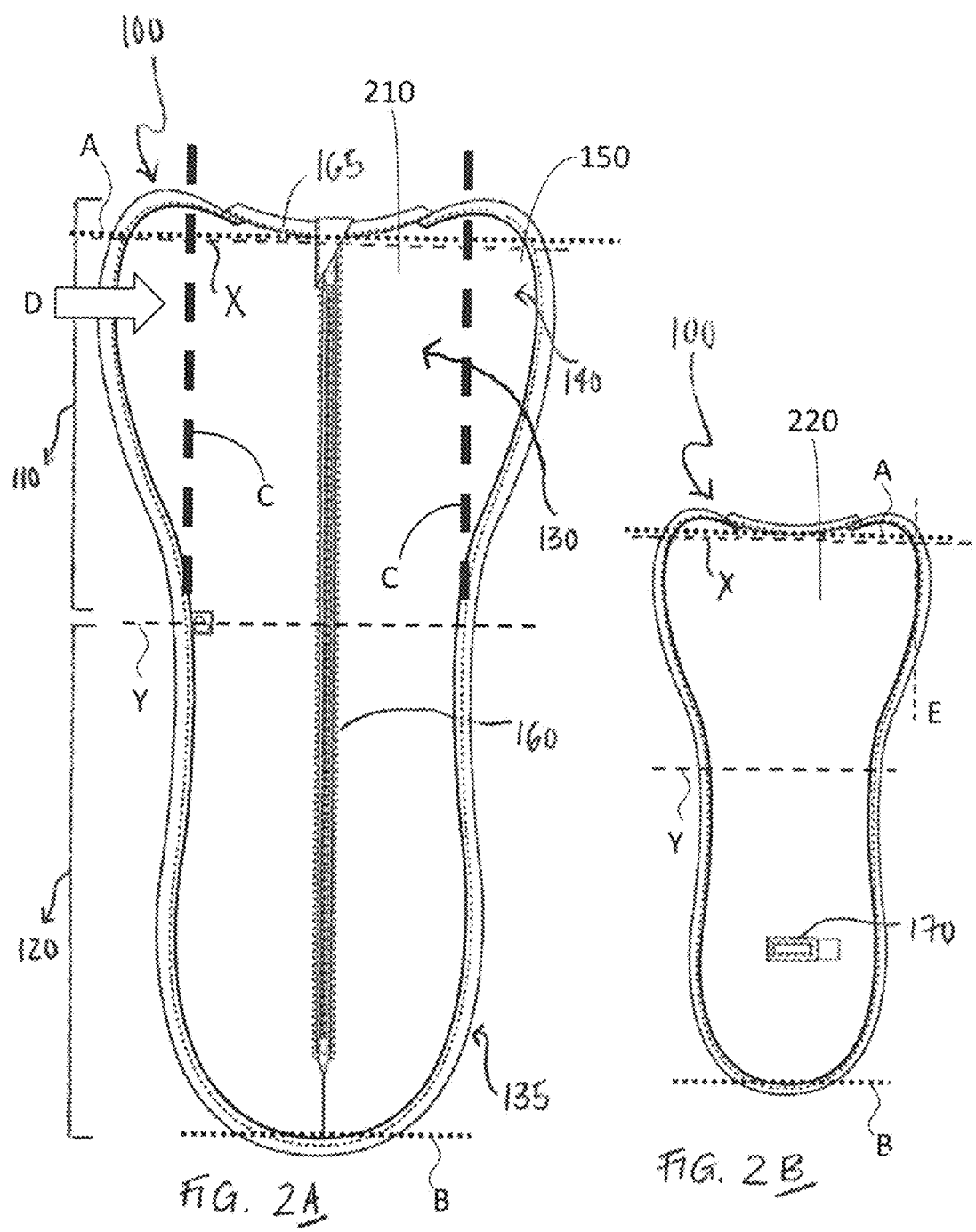
FIG. 2A is a front view of an alternate embodiment.
FIG. 2B is a back view of the alternate embodiment shown in FIG. 2A, shown in a smaller scale.
Figure 3:
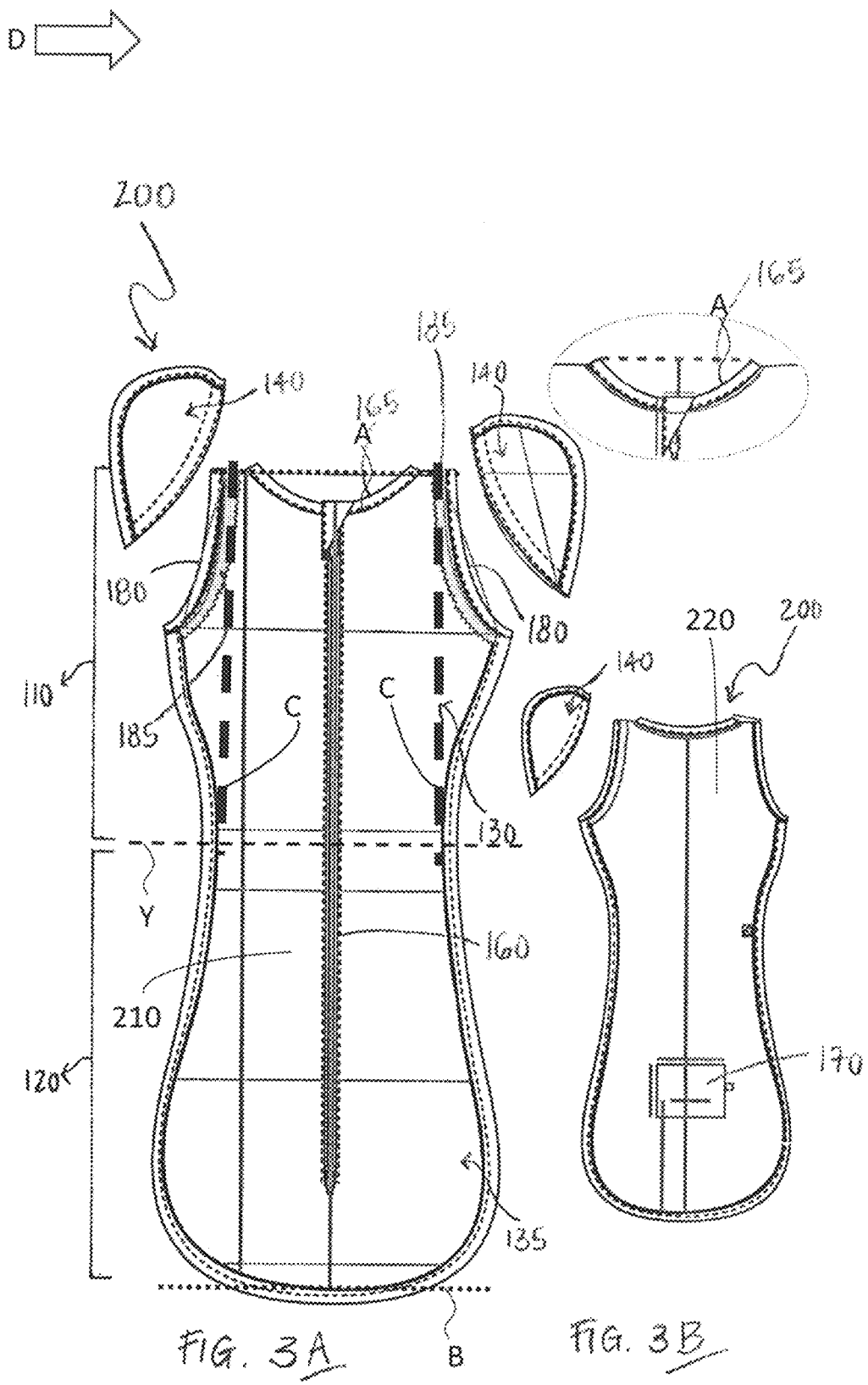
FIG. 3A is a front view of another alternative embodiment.
FIG. 3B is a back view of the alternative embodiment of FIG. 3A, shown in a smaller scale.

Referring to FIGS. 2A and 2B, an alternative arrangement of the embodiment illustrated in FIGS. 1A and 1B is shown, in which the swaddling garment 100 has wing tips 150 that clearly extend above the shoulder line (the approximate position of the shoulder line is demarcated by the dashed line labelled X in FIGS. 2A and 2B). It can be seen by comparing FIGS. 1A to 2B that the wing tip 150 (i.e. the most lateral portion of the wing portion 140) may be shaped to accommodate the hands to the sides of the bodice portion 130 (FIGS. 1A, 1B and 2A and 2B) as well as substantially near the shoulder line (FIGS. 1A and 1B) or above the shoulder line (FIGS. 2A and 2B). The embodiment of FIGS. 2A and 2B otherwise retains the same features as the embodiment depicted in FIGS. 1A and 1B.

Referring to FIGS. 3A, 3B and 4, an alternative embodiment 200 is shown in which at least part of each wing portion 140 is detachable from the bodice portion 130. FIGS. 3A and 3B show the wing portions 140 detached while FIG. 4 shows the wing portions 140 attached. The detachable wing portions 140 can be fastened to the bodice portion using any suitable fastening means, such as the hook and loop fasteners shown in FIG. 3A labelled item 185 or a zipper means.

Removal of the wing portions 140 leaves an armhole (opening) 180 on either side of the bodice portion 130 (see FIGS. 3A and 3B). An infant wearing the swaddling garment 200 is able to become unswaddled by extending one or both arms laterally out from the garment through the opening(s) 180. This embodiment 200 assists parents to transition the infant out of swaddling by removing a first wing portion 140 and leaving the second wing portion attached so that one of the infant's arms is still maintained in the elbows-bent-and-hands-raised position. The swaddling garment 200 is used in this manner for a transition period (e.g. a few weeks) to allow the infant to accommodate to having one arm completely out and free to move. The next step is to remove the second wing portion, in which case the infant is no longer swaddled and the garment 200 acts like a sleeping bag.

In the embodiment 200 shown in FIGS. 3A, 3B, and 4, the lower portion 120 is shaped so that it is wider at its lowermost end than around the waist. This is in contrast to the embodiment 100 of FIGS. 1A and 1B and 2A and 2B, in which the lower portion tapers in below the wing portion then expands to accommodate the hip and then remains substantially the same width down to the feet. The shape of the lower portion 120 of the embodiment 200 of FIGS. 3A, 3B, and 4 allows a greater degree of freedom of movement of the lower limbs than the first embodiment, which reflects use of this embodiment 200 in infants being prepared for transition out of swaddling. The embodiment 200 of FIGS. 3A, 3B, and 4 otherwise retains the same features of the embodiment 100 described in relation to FIGS. 1A and 1B and 2A and 2B. Items bearing the same item label in different figures depict the same feature in different arrangements/embodiments. The features of embodiment 200 are otherwise as described for embodiment 100 illustrated in FIGS. 1A and 1B.

Referring to FIGS. 5A and 5B, a third embodiment 300 is shown, in which the position-restricting means that retains the hands near the face includes:

1. wing portions 140 configured to receive the arms in a hand-raised position, with the hands raised near, towards or above the shoulder line; and
2. a tension pouch 190 intermediate each wing portion 140 and the bodice portion 130, near or towards the horizontal plane of the shoulder line (indicated by line "X" in FIGS. 5A and 5B).

In this embodiment 300, the most lateral part of the wing portions 140 act like sleeves to receive the lower arms. The "ends" (most lateral part) of the wing portions 140 may be open, allowing the hands to extend through the open end. Alternatively, the ends of the wing portions 140 may be closed so that the hands are retained within the wing portions 140. In contrast to the embodiments 100 and 200 of FIGS. 1A to 4, the embodiment 300 of FIGS. 5A and 5B relies on tension to resist the arms and hands moving away from the bodice portion, rather than pressure to tend the arms and hands toward the face. When the wing portions 140 are open, the arms may extend up through the wing portion resulting in the elbow being extended away from the bent position. However, the hand is still retained in position relative to the face and accessible to the mouth by virtue of the tension pouch 190. The embodiment of FIGS. 5A and 5B otherwise retains the same features as the embodiment depicted in FIGS. 1A and 1B.

Referring to FIGS. 6A and 6B, front and back views of yet another embodiment are shown. This embodiment includes weighted portions or areas (cross-hatched in FIGS. 6A-6E and 7A-7F) to apply additional pressure on or around the belly region to assist in relieving the symptoms of colic. This feature (applying gentle pressure around the horizontal plane of the abdomen area) is achieved through the combination of:

(a) weighted portions (areas shown with cross-hatching in FIGS. 6A and 6B, and 7A to 7F) around the parts of the garment 600 that sit around the abdomen;

(b) tapering in of the garment 600 below the wing portions 140 at the garment waistline (demarcated by line "Y") so that the garment is narrower around the abdomen area than between the wing portions 140.

The embodiment of FIGS. 6A-6E and 7A-7F has the same features as described in relation to the embodiments of FIGS. 1A and 1B and 2A and 2B. The wing portions 140 are shown extending laterally from each side of the bodice portion 130. The lower portion may take various forms—from a sack-like shape for accommodating both legs (tapered in or out, as shown by way of example in FIGS. 7A and 7B), to an open portion so that the garment 600 takes the form of an elongated swaddling jacket (FIG. 7D), or a "onesie"-style garment with leg openings (FIG. 7E), short pants (FIG. 7F) or long pants (FIG. 7C—shown as footed pants, but could also be open at the feet).

The weighted portions (FIGS. 8A to 8D) are configured to apply gentle pressure to the abdomen, to help soothe a colicky infant. This is through the positioning of the weighted portions over the portions of the garment that correspond to the abdomen—on both the front panel 210 and back panel 220 of the garment 600.

Cross-sections of the embodiment of FIGS. 6A and 6B are shown in FIGS. 6C to 6E. FIGS. 6A, 6B and 8A to 8D show that the weighted portions may extend up over the garment waistline to just under the diaphragm, and down to the lowermost periphery/edge of the garment (demarcated by line "B"). As can be seen from the cross-sections in FIGS. 6C to 6E, the part of the upper portion 110 of the garment including the wing portions 140 is made of a single layer of fabric—for comfort. The wing portions 140 secure the infant's arms but allow access to the hands for non-nutritive sucking. By contrast, the weighted portions (the cross-hatched areas) are made from material with a higher thermal weight and, as such, form (a) semi-rigid portion(s) of the garment compared with the wing portions 140. This semi-rigid portion applies gentle pressure to the abdomen areas of an infant within the garment 600. The weighted portion may be made of a material with a greater thermal weight than the non-weighted portion or, as illustrated in FIGS. 6C to 6E, include two or more layers of fabric. In an arrangement, the weighted portion further includes a layer of insulation between two of the layers of fabric so that the weighted portions form an in-built quilted portion of the garment.

FIGS. 8A to 8D show that the precise shape and arrangement of weighted portions may vary. The shape of the weighted portion may be parabolic across the upper abdomen (as shown in FIGS. 6A and 6B), a gentle curve corresponding to the lower ribs, straight across the horizontal plane of the upper abdomen (see FIG. 8A), or a 2D shape sitting over the abdomen and extending down to the lower portion (e.g. an oval as in FIG. 8B, or a rectangle as in FIGS. 8C and 8D). Further the weighted portion on a single panel (front panel 210 or back panel 220) may be made up of more than one shape (e.g. as shown in FIG. 8D in which a first weighted portion sits over the abdomen and a second weighted portion sits lower down the lower portion—for warmth).

The weighted portions (cross-hatched areas of FIGS. 6A-6E, 7A-7F, and 8A-8D) have higher thermal weight and/or material weight than the non-weighted portions (the areas not shaded in FIGS. 6A to 8D). The weighted portions are configured to sit over the abdomen area on the front panel 210 and back panel 220 of the garment 600, and to apply pressure through the weight of the fabric to the infant within.

For comfort, the garment 600 includes areas of different thermal (or material weight), with:

(a) weighted portions of the garment (cross-hatched areas in FIGS. 6A to 8D) that are semi-rigid relative to the non-weighted portions, to apply gentle pressure to the abdomen area to comfort and soothe the infant; and (b) non-weighted portions (areas not cross-hatched in FIGS. 6A to 8D) that are flexible relative to the weighted portions, for comfort and to allow movement/access of the hand to the mouth for non-nutritive sucking.

As can be seen from FIGS. 6A to 8D, the uppermost portion of the upper portion 110 (including the wing portions 140 and the part of the bodice portion 130 between the wing portions 140) do not include weighted portions. This can be seen from FIG. 6C (as shown in cross section across line F-F). This allows the non-weighted areas of the garment 600 to be more flexible relative to the part(s) of the garment that include weighted portions. For similar reason, the garment includes areas of lighter thermal weight for comfort at the sides of the garment—as can be seen in FIGS. 6A to 8D. The areas of lighter thermal weight may be only around the wing portions (e.g. FIGS. 6A to 6E, 8A), along the sides of the garment from the uppermost to lowermost peripheries (e.g. FIGS. 8B, 8C and 8D), or additionally also in parts of the lower portion (e.g. FIG. 8D).

As can be seen from FIGS. 6D and 6E, the garment 600 applies gentle pressure equally around the abdomen area. This is achieved by having the same thermal weight or material weight in the front panel 210 and back panel 220. Accordingly, as can be seen from FIGS. 6D and 6E, a weighted portion placed centrally on the abdomen in the front panel is countered by a weighted portion of equivalent thermal weight positioned correspondingly in the back panel.

The garment (in all embodiments) is designed to fit snugly around the contours of an infant and in this way applies pressure around the abdomen area of an infant enclosed therein—even in the absence of weighted portions. The weighted portions enhance this effect. In the embodiments depicted in FIGS. 6A and 6B and 7A, the garment waist line demarcated by line "Y" represents a notional division between the upper portion and lower portion of the garments. As with the embodiments in FIGS. 1A to 5B, the garment tapers in below the wing portions to hug the torso around the abdomen area (the part of the garment notionally corresponding to the region between the thorax to the pelvis).

Method of Swaddling an Infant

The invention also provides a new or alternative method of swaddling an infant using a swaddling garment that improves protection against SIDS by facilitating non-nutritive sucking.

A specific example is provided below.

Example 1

The example relies on a swaddling garment that retains the hands near the face and that sufficiently restricts movement of the limbs to suppress the startle reflex, while allowing baby movement of hand to mouth.

Using the embodiment 100 illustrated in FIGS. 1A and 1B:

1. Insert the infant's torso and arms through the opening into the upper portion of the swaddling garment;
2. Insert the arms up into the wing portions;
3. Tuck the hands into the wing tip;
4. Close the opening of the garment by closing the closure means.
5. A further step of inserting an infant's legs through the opening of the garment, so that the legs are received by the pouch (optional).

An advantage of any of the preferred embodiments is that the swaddling garment swaddles infants by sufficiently restraining movement of the limbs to suppress the startle reflex, yet allowing movement of the hand towards the mouth and maintaining the hand in position relative to the infant's face such that the hands are accessible to the mouth. The relative positioning of the hands to the mouth facilitates non-nutritive sucking and restricts movement of the arms and hands away from this position. In this way, the swaddling garment offers advantages over other swaddling garments by providing greater protection against sudden infant death syndrome (SIDS) by virtue of facilitating non-nutritive sucking in combination with the advantages of swaddling.

A further advantage of the preferred embodiments is that the swaddling garment facilitates non-nutritive sucking without relying on a pacifier.

Yet another advantage of the swaddling garment is that the arms are semi-restrained in a position that reduces the risk of the swaddled infant rolling over into the prone position from the supine position. If the infant does roll onto his or her front, the hands are positioned so they are available to the infant (rather than being bound to the body) to push him- or herself up at least so the infant can lift the head and turn it to the side, or even to push him- or herself back into a supine position, thereby minimising the risk of suffocation. This is further protective against the risk of SIDS.

Another advantage still of the swaddling garment is that the garment provides gentle pressure around the torso (and specifically the abdomen area) to help relieve the symptoms of colic and to soothe the baby within. The relative difference in rigidity between the weighted and non-weighted portions allows pressure to be differentially applied without discomfort or limiting access to mouth for non-nutritive sucking.

The invention provides a swaddling garment for use in swaddling infants and which assists to protect against SIDS by facilitating non-nutritive sucking in combination with the advantages of swaddling. The swaddling garment has been developed primarily for use as a means for swaddling infants for safe sleeping. However, it will be appreciated that the invention is not restricted to these particular fields of use and that it is not limited to particular embodiments or applications described herein.

I claim:

1. A swaddling garment for swaddling an infant, including:
    an upper portion for enclosing the torso and arms of the infant, wherein the upper portion includes:
    (a) a bodice portion sized to enclose the torso of the infant, and
    (b) two wing portions, each of the two wing portions extending laterally from a respective side of the bodice portion at an uppermost portion of the swaddling garment, wherein the bodice portion is positioned intermediate the two wing portions, each wing portion of the two wing portions having a wing tip at an uppermost portion of the wing portion; and (c) a neck hole positioned at a central region of the uppermost portion of the swaddling garment, the neck hole having a lowermost point through which a shoulder line of the bodice portion extends, wherein each of the two wing portions is configured to completely surround and retain an arm and hand of the infant in a hand-raised and elbow-bent position to at a respective side of the infant, wherein the wing tip of each of the two wing portions extends above the shoulder line of the bodice portion;

the swaddling garment being tapered in at a waistline below each of the two wing portions and configured to restrict movement of the arms of the infant out of the two wing portions and into the bodice portion, wherein the swaddling garment is configured to hold each of the arms of the infant in a respective one of the two wing portions while allowing movement of the hands of the infant to the mouth of the infant while retaining the arms and hands in the two wing portions.

2. The swaddling garment according to claim 1, wherein the bodice portion includes a front panel and a back panel, each of the front and the back panels portions including a weighted portion and a non-weighted portion, wherein the weighted portion is configured to apply pressure around a horizontal plane corresponding to the abdomen of the infant.

3. The swaddling garment according to claim 2, wherein the non-weighted portion consists of a single layer of fabric for comfort and flexibility.

4. The swaddling garment according to claim 2, wherein the weighted portion is of a greater thermal weight than the non-weighted portion, such that the weighted portion of the swaddling garment is semi-rigid relative to the non-weighted portion.

5. The swaddling garment according to claim 2, wherein the weighted portion includes two or more layers of fabric.

6. The swaddling garment according to claim 2, wherein the weighted portion further includes a layer of insulation between two of the layers of fabric.

7. The swaddling garment according to claim 1, wherein a width of the swaddling garment between the two wing portions is greater than a width of the swaddling garment at the waistline so that the swaddling garment is configured to inhibit movement of the infant from a supine position to a prone position.

8. The swaddling garment according to claim 7, wherein the swaddling garment is rounded to follow contours of the infant.

9. The swaddling garment according to claim 1, wherein each of the two wing portions further includes a pocket, wherein the pocket is configured to enclose a hand of the infant.

10. A The swaddling garment according to claim 9, wherein the pocket is configured to enclose a lower arm and hand of the infant.

11. The swaddling garment according to claim 1, wherein the garment is notionally demarcated into upper and lower portions by the waistline, wherein the garment has an uppermost periphery at an uppermost end of the upper portion, and a lowermost periphery at a lowermost end of the lower portion, wherein each of the two wing portions extends substantially from the uppermost periphery to the waistline, and wherein a distance as measured from a most lateral part of one of the two wing portions to the waistline is smaller than a distance as measured from the uppermost periphery of the swaddling garment to the waistline, such that the two wing portions are configured to restrict movement of the arms of the infant away from the bodice portion while allowing movement of the hands of the infant towards the mouth of the infant.

12. The swaddling garment according to claim 1, wherein the upper portion further includes a tension pouch intermediate each wing portion and the bodice portion near the shoulder line, wherein the tension pouch is configured to bias an arm of the infant toward the elbow-bent and-hand-raised position such that the hand is retained in a position accessible to the mouth when in one of the two wing portions.

13. The swaddling garment according to claim 1, wherein each of the two wing portions is detachable from the bodice portion, wherein detaching one of the two wing pardon portions leaves an opening at the respective side of the bodice portion, wherein the opening is configured such that the infant is able to extend an arm out of the swaddling garment through the opening.

14. The swaddling garment according to claim 1, wherein the swaddling garment is made of a material comprising elasticated yarn.

15. A The swaddling garment according to claim 1, wherein the swaddling garment further includes a lower portion configured for enclosing the lower body of the infant.

16. A swaddling garment according to claim 1, wherein each of the two wing portions comprises a resilient material, wherein the resilient material is a fabric having an ability to stretch and return to its original position.

17. A swaddling garment for swaddling an infant, comprising:

an upper portion for enclosing the torso and arms of the infant, wherein the upper portion includes:

(a) a bodice portion, and (b) two wing portions, each of the two wing portions extending laterally from a side of the bodice portion;

wherein each of the two wing portions is configured to completely surround and retain an arm and hand of the infant in a hand-raised and elbow-bent position at a respective side of the infant, each wing portion of the two wing portions having a wing tip at an uppermost portion of the wing portion, wherein the wing tip of each of the two wing portions extends above a shoulder line of the upper portion, (c) a neck hole positioned at a central region of an uppermost portion of the swaddling garment, the neck hole having a lowermost point through which the shoulder line of the upper portion extends, the swaddling garment being tapered in at a waistline below the two wing portions to restrict movement of the arms of the infant out of the two wing portions and into the bodice portion, and wherein the swaddling garment is configured to hold the arms and hands of the infant in the two wing portions and to each side of the bodice portion while allowing sufficient movement of the hands to the mouth of the infant while the arms and hands of the infant are retained in the two wing portions of the swaddling garment.

18. The swaddling garment according to claim 17, wherein each of the two wing portions is configured to be resilient to bias an arm of the infant toward the bodice portion such that each of the two wing portions is configured so that once each arm is in the elbow-bent-and-hand-raised position, the two wing portions maintain the hands near the mouth of the infant.

19. The swaddling garment as defined in claim 17, wherein the swaddling garment includes an uppermost periphery at an uppermost end of the upper portion, and a lowermost periphery at a lowermost end of a lower portion,
 wherein each of the two wing portions extend substantially from the uppermost periphery to the waistline, and
 wherein a distance as measured from a most lateral part of each of the two wing portions to the waistline is smaller than a distance as measured from the uppermost periphery of the swaddling garment to the waistline, such that the two wing portions are configured to restrict movement of the arms of the infant away from the bodice portion while allowing movement of the hands of the infant towards the mouth of the infant, and
 wherein the upper portion tapers in at the waistline below each of the two wing portions, thereby preventing passage of the arms out of the two wing portions and into the bodice portion such that the hands of the infant are retained in a position within the two wing portions when accessible to the mouth.

20. A swaddling garment according to claim 17, wherein each of the two wing portions comprises a resilient material, wherein the resilient material is a fabric having an ability to stretch and return to its original position.

21. A method for swaddling an infant including the step of inserting the infant into a swaddling garment, the garment having an upper portion for enclosing the torso and arms of the infant, wherein the upper portion includes:
 (a) a bodice portion sized to enclose the torso of the infant, and
 (b) two wing portions, each extending laterally from a respective side of the bodice portion at an uppermost portion of the swaddling garment, each of the two wing portions being configured to completely surround and retain an arm and hand of the infant in a hand-raised and elbow-bent position at a respective side of the bodice portion;
 each wing portion of the two wing portions having a wing tip at an uppermost portion of the wing portion; and
 (c) a neck hole positioned at a central region of the uppermost portion of the swaddling garment, the neck hole having a lowermost point through which a shoulder line of the upper portion extends,
 wherein the swaddling garment is configured to hold the arms of the infant in the two wing portions to each side of the bodice portion and allow sufficient movement of the arms to the mouth while the arms are retained in the two wing portions.

22. The method of claim 21, further comprising placing a first of the infant's arms into a first wing portion of the two wing portions and placing a second of the infant's arms into a second wing portion of the two wing portions to restrict movement of the infant's arms away from the bodice portion while maintaining the infant's arms and hands raised in position and accessible to the mouth while retained in the two wing portions.

\* \* \* \* \*

UNITED STATES PATENT AND TRADEMARK OFFICE
CERTIFICATE OF CORRECTION

PATENT NO. : 11,357,268 B2
APPLICATION NO. : 14/935929
DATED : June 14, 2022
INVENTOR(S) : Hana-Lia Krawchuk It is certified that error appears in the above-identified patent and that said Letters Patent is hereby corrected as shown below:

In the Claims

In Claim 1 on Column 17, Line 10, delete "position to" and insert --position--.

In Claim 2 on Column 17, Line 26, delete "panels portions" and insert --panels--.

In Claim 6 on Column 17, Line 42, delete "two of the layers" and insert --two layers--.

In Claim 10 on Column 17, Line 56, delete "A The" and insert --The--.

In Claim 13 on Column 18, Line 19, delete "wing pardon" and insert --wing--.

In Claim 15 on Column 18, Line 27, delete "A The" and insert --The--.

Signed and Sealed this
Sixteenth Day of August, 2022

Katherine Kelly Vidal
*Director of the United States Patent and Trademark Office*